(12) United States Patent
Kim et al.

(10) Patent No.: US 11,484,315 B2
(45) Date of Patent: Nov. 1, 2022

(54) STENT FOR ANASTOMOSIS OF DIFFERENT KINDS OF ORGANS

(71) Applicants: THE ASAN FOUNDATION, Seoul (KR); UNIVERSITY OF ULSAN FOUNDATION FOR INDUSTRY COOPERATION, Ulsan (KR)

(72) Inventors: Song-Cheol Kim, Seoul (KR); Chang Mo Hwang, Seoul (KR); In Kyong Shim, Seoul (KR); Jung-Hoon Park, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 345 days.

(21) Appl. No.: 16/608,433

(22) PCT Filed: Apr. 27, 2018

(86) PCT No.: PCT/KR2018/004918
§ 371 (c)(1),
(2) Date: Oct. 25, 2019

(87) PCT Pub. No.: WO2018/199683
PCT Pub. Date: Nov. 1, 2018

(65) Prior Publication Data
US 2020/0046357 A1   Feb. 13, 2020

(30) Foreign Application Priority Data
Apr. 27, 2017 (KR) .................. 10-2017-0054622

(51) Int. Cl.
*A61B 17/11* (2006.01)
*A61B 17/04* (2006.01)
*A61F 2/04* (2013.01)

(52) U.S. Cl.
CPC ...... *A61B 17/1114* (2013.01); *A61B 17/0485* (2013.01); *A61F 2/04* (2013.01); *A61B 2017/1132* (2013.01); *A61F 2002/041* (2013.01)

(58) Field of Classification Search
CPC . A61B 17/11; A61B 17/1114; A61B 17/0485; A61B 2017/1132; A61F 2/01;
(Continued)

(56) References Cited

U.S. PATENT DOCUMENTS 5,478,353 A * 12/1995 Yoon .................. A61B 17/0057
606/220
5,904,697 A * 5/1999 Gifford, III ...... A61B 17/12109
606/155

(Continued)

FOREIGN PATENT DOCUMENTS

JP  2007-503279 A  2/2007
JP  2009-525775 A  8/2007

(Continued)

OTHER PUBLICATIONS

Translation of International Search Report dated Aug. 6, 2018 and Written Opinion in corresponding International Application No. PCT/KR2018/004918; 20 pages.

*Primary Examiner* — Diane D Yabut
(74) *Attorney, Agent, or Firm* — Maier & Maier, PLLC

(57) ABSTRACT

A stent for anastomosis of different kinds of organs includes a main body, and at least one fixing unit provided in the main body. At least a portion of the main body is inserted into one of different kinds of organs to be anastomosed with each other, and the rest of the main body is inserted into the other of the different kinds of organs. A distance between the different kinds of organs under the anastomosis is maintained by the fixing units.

14 Claims, 19 Drawing Sheets

(58) Field of Classification Search
CPC .................. A61F 2/04; A61F 2002/041; A61F 2002/8483; A61F 2/0103; A61F 2/0105; A61F 2/848; A61F 2220/0008; A61F 2220/0016

See application file for complete search history.

(56) References Cited

U.S. PATENT DOCUMENTS

| | | | |
|---|---|---|---|
| 6,217,600 B1 * | 4/2001 | DiMatteo | A61F 2/0105 606/198 |
| 6,666,873 B1 | 12/2003 | Cassell | |
| 8,845,663 B2 | 9/2014 | Chmura | |
| 2001/0047180 A1 | 11/2001 | Grudem et al. | |
| 2009/0318951 A1 * | 12/2009 | Kashkarov | A61F 2/0105 606/200 |
| 2010/0016882 A1 * | 1/2010 | Lapid | A61F 2/0105 606/200 |
| 2010/0082049 A1 * | 4/2010 | Orban, III | A61B 17/064 606/153 |
| 2015/0245839 A1 | 9/2015 | Wirtel, III et al. | |

FOREIGN PATENT DOCUMENTS

| | | |
|---|---|---|
| KR | 10-2001-0017739 A | 3/2001 |
| KR | 10-0340336 B1 | 6/2002 |

* cited by examiner (A – A')

STENT FOR ANASTOMOSIS OF DIFFERENT KINDS OF ORGANS

FIELD

The present invention relates to a stent for anastomosis of different kinds of organs.

BACKGROUND

In general, a stent is used to expand the stenosis site, and is manufactured for proper use depending on the size, nature and environment of the various organs and lumens to be installed.

Recently, researches have been conducted to use the stent not only to expand the stenosis site, but also to guide the movement paths of various surgical instruments through the expansion of the organs and the lumens or generate additional movement paths of the surgical instruments to connect different kinds of organs.

Among them, in particular, there have been actively made the researches on pancreatojejnnostomy for anastomosis of the pancreatic duct and the digestive tract (jejunum) and choledocho hepaticojejunostomy for anastomosis of the biliary tract and the jejunum for the purpose of eliminating pain and recovering exocrine function, in case the main pancreatic duct is closed and the expanding or endocrine function remains at its end after the resection of a liver or a pancreas or due to diseases such as acute/chronic pancreatitis, pancreatic vesicle, pancreatic fistula, and pancreatic trauma.

As such, Korean Patent Laid-open Publication No. 10-2013-0110413 entitled "Stent for anastomosis" has proposed to use a stent for purposes other than the expansion of the stenosis site. The stent for anastomosis disclosed in Korean Patent Laid-open Publication No. 10-2013-0110413 is configured to splice different kinds of organs by being inserted into through-holes formed separately in the different kinds of organs.

However, due to the flexibility of the organs, it is very difficult to keep the different kinds of organs in close contact with each other during surgery, so that positions of the through-holes formed in the different kinds of organs are frequently displaced. Therefore, there is an urgent need to provide a unit for fixing the position of the stent for anastomosis after it is inserted into the through holes.

In addition, a stent of a diameter of about 2 mm having a very small size may be used, which makes it very difficult to connect the organ to the organ using such small stent, thereby causing a long operation time and an excessive fatigue for the surgeon.

SUMMARY

Embodiments of the present invention have been proposed in view of the problems of the prior arts as described above, and thus are intended to provide a stent for anastomosis of different kinds of organs, which can anastomose the different kinds of organs quickly and conveniently and minimize surgical complication by maintaining a close contact between the different kinds of organs to be anastomosed when a pancreatojejnnostomy or a choledocho hepaticojejunostomy is performed.

In accordance with an aspect of the present disclosure, there is provided a stent for anastomosis of different kinds of organs, including: a main body; and at least one fixing unit provided in the main body, wherein at least a portion of the main body is inserted into one of different kinds of organs to be anastomosed with each other, and the rest of the main body is inserted into the other of the different kinds of organs, and wherein a distance between the different kinds of organs under the anastomosis is maintained by the fixing units.

The at least one fixing unit may include one or more hook members installed on an outer circumferential surface of the main body, and each of the one or more hook members may include an extension portion outwardly extending from an outer circumferential surface of the main body; a locking portion formed at an end portion of the extension portion and having a shape with which the different kinds of organs are latched; and a recess groove recessed between the extension portion and the locking portion.

The one or more hook members may include one or more pairs of the hook members, and end portions of the same pair of hook members may be extended away from each other in a longitudinal direction of the main body so that the end portions are fixedly latched to the different kinds of organs.

The locking portion may have a hook shape in which a diameter becomes smaller as goes away from the end portion of the extension portion.

The at least one fixing unit may include a ring member installed on an outer circumferential surface of the main body to pass a suture thread for suturing a gap to be formed between the different kinds of organs.

The at least one fixing unit may include a plurality of through-holes which are formed on an outer circumferential surface of the main body to pass a suture thread for suturing a gap to be formed between the different kinds of organs.

The at least one fixing unit may include: a ring member installed on an outer circumferential surface of the main body to pass a suture thread for suturing between the different kinds of organs; and a plurality of through-holes which are formed on an outer circumferential surface of the main body to pass a suture thread for suturing a gap to be formed between the different kinds of organs.

The at least one fixing unit may include: one or more hook members installed on an outer circumferential surface of the main body; and at least one of a ring member and a plurality of through-holes through which a suture thread for suturing a gap to be formed between the different kinds of organs passes, wherein the at least one of the ring member is installed on the outer circumferential surface of the main body, and the plurality of through-holes are formed on the outer circumferential surface of the main body.

The one or more hook members may include a plurality of hook members, and the plurality of hook members are arranged along a circumferential direction of the main body to have an equal interval between each hook member and its adjacent hook member.

The at least one fixing unit may include the ring member, and the ring member may be arranged at a position to face the plurality of hook members.

The main body may include a first body to be inserted into one of the different kinds of organs; and a second body to be inserted into the other of the different kinds of organs and detachably coupled to the first body.

The main body may further include: a locking piece provided in one of the first body and the second body; and an insertion groove into which the locking piece is inserted and provided in the other of the first body and the second body.

A locking jaw to which the locking piece is fixedly latched may protrude from an inner circumferential surface of the insertion groove, and the different kinds of organs may be maintained to make a contact with each other when the locking piece is fixedly latched to the locking jaw.

The main body and the at least one fixing unit may include a biodegradable polymer including one or more species selected from a group consisting of polyglycolide, polylactide (PLLA), polylactide-glycolide copolymer (PLGA), poly p-dioxanone, polycaprolactone, trimethylene carbonate (TMC), polydioxanone-trimethylene carbonate-polyglycolide tri-block copolymer, polyhydroxyalkanoate, polypropylene fumarate, polyortho ester, polyester, polyanhydride, polyphosphazenes, polyalkylcyanoacrylate, poloxamer, polyamino L-tyrosine, modified polysaccharride, oxidized cellulose, gelatin and collagen.

The main body may have a hollow cylindrical shape one end of which is to be inserted inside one of the different kinds of organs and the other end of which is to be inserted inside the other of the different kinds of organs to communicate between the different kinds of organs.

A stent for anastomosis of different kinds of organs according to embodiments of the present invention has the effect which is capable of anastomosing the different kinds of organs quickly and conveniently and minimizing surgical complication by maintaining a close contact between the different kinds of organs to be anastomosed when a pancreatojejnnostomy or a choledocho hepaticojejunostomy is performed.

DETAILED DESCRIPTION

Figure 1:
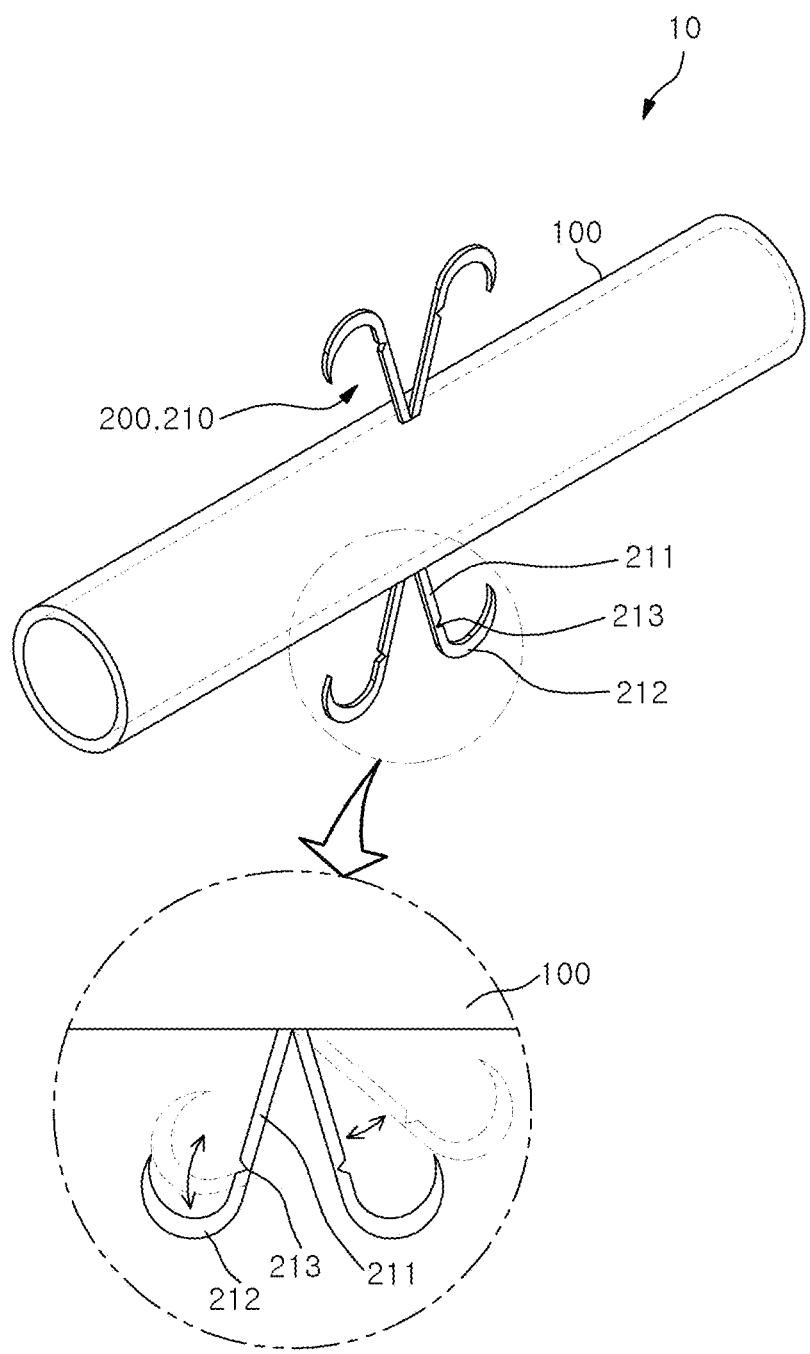
FIG. 1 is a perspective view showing an example of a stent for anastomosis of different kinds of organs according to a first embodiment of the present invention.

Hereinafter, configurations and operations of embodiments will be described in detail with reference to the accompanying drawings. The following description is one of various patentable aspects of the disclosure and may form a part of the detailed description of the disclosure. However, in describing the disclosure, detailed descriptions of known configurations or functions may be omitted to not obscure the disclosure.

The disclosure may be variously modified and may include various embodiments. Specific embodiments will be exemplarily illustrated in the drawings and described in the detailed description of the embodiments. However, it should be understood that they are not intended to limit the disclosure to specific embodiments but rather to cover all modifications, similarities, and alternatives which are included in the spirit and scope of the disclosure.

The terms used herein, including ordinal numbers such as "first" and "second" may be used to describe, and not to limit, various components. The terms simply distinguish the components from one another. When it is said that a component is "connected" or "linked" to another component, it should be understood that the former component may be directly connected or linked to the latter component or a third component may be interposed between the two components. Specific terms used in the present application are used simply to describe specific embodiments without limiting the disclosure. An expression used in the singular encompasses the expression of the plural, unless it has a clearly different uniting in the context.

Figure 2:
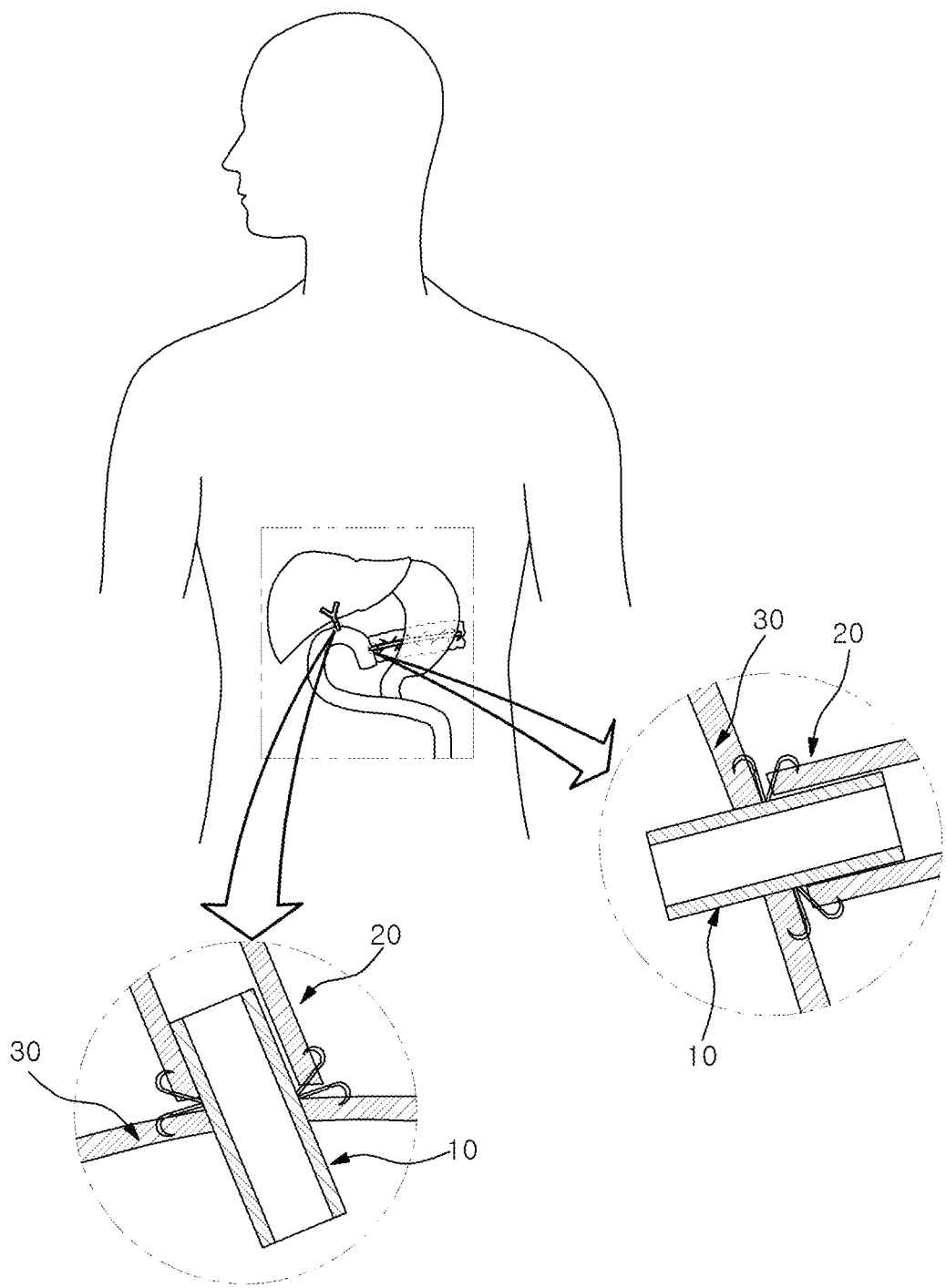
FIG. 2 is a view showing the stent for anastomosis of the different kinds of organs of FIG. 1 applied to a human body.

Referring to FIGS. 1 and 2, a stent 10 for anastomosis of different kinds of organs according to an embodiment of the present invention is a medical device that can be used to anastomose the different kinds of organs. Hereinafter, a case in which the stent 10 for anastomosis of the different kinds of organs is used in pancreatojejnnostomy connecting a pancreatic duct and a jejunum and choledocho hepaticojejunostomy connecting a biliary tract and the jejunum will be described as an example.

The stent 10 for anastomosis of the different kinds of organs according to an embodiment of the present invention may include a main body 100 and at least one fixing units 200.

The main body 100 may connect the different kinds of organs, e.g., a first organ 20 and a second organ 30 and provide a passage through which body fluids such as pancreatic fluid or bile can move. For this purpose, at least a part of the main body 100 may be inserted inside the first organ 20, and the rest of the main body 100 may be inserted inside the second organ 30.

Such main body 100, for example, may be formed in a hollow cylindrical shape having a diameter of 0.5 mm to 5 mm, a length of 10 mm to 60 mm, and a thickness of 0.1 mm to 0.2 mm or less, but this is merely example and the diameter, the length and the thickness of the main body 100 can be variously modified depending on the organs to be inserted.

In addition, the main body 100 may be made of a biodegradable polymer including one or more species selected from the group consisting of polyglycolide, polylactide (PLLA), polylactide-glycolide copolymer (PLGA), poly p-dioxanone, polycaprolactone, trimethylene carbonate (TMC), polydioxanone-trimethylene carbonate-polyglycolide tri-block copolymer, polyhydroxyalkanoate, polypropylene fumarate, polyortho ester, other polyesters, polyanhydride, polyphosphazenes, polyalkylcyanoacrylate, poloxamer, polyamino L-tyrosine, modified polysaccharides, oxidized cellulose, gelatin and collagen. Such main body 100 may be absorbed into a human body within a predetermined period, for example, 1 month to 3 months.

The fixing units 200 may maintain a distance between the first organ 20 and the second organ 30, which is closely adhered to by a surgeon in order to anastomose the first organ 20 and the second organ 30.

To this end, the fixing units 200 include at least one or more of a hook member 210, a ring member 220 and a plurality of through holes 230, and the present embodiment will describe as an example the case in which the fixing units 200 includes the hook member 210.

The hook member 210 may be provided in at least one pair on an outer circumferential surface of the main body 100. For example, the hook member 210 may be formed in a shape that can be latched by the first organ 20 and the second organ 30.

In this case, end portions of the pair of the hook members 210 may be formed to extend laterally in a direction away from each other so that the end portions are fixedly latched to the first organ 20 and the second organ 30. Accordingly, by the pair of the hook members 210 secured to the first organ 20 and the second organ 30, the distance between the first organ 20 and the second organ 30, which is arbitrarily in close contact with each other by the surgeon, may be maintained in close contact until the surgery is completed, for example, until the suture of the first organ 20 and the second organ 30 is completed.

For this purpose, each of the hook members 210 may include an extension portion 211, a locking portion 212 and a recess groove 213.

The extension portion 211 is the part outwardly extending from the outer circumferential surface of the main body 100, and may, for example, be formed in a cylindrical shape. In this case, the extension portion 211 may outwardly extend to incline at a predetermined angle with respect to the outer circumferential surface of the main body 100, but this is merely an example and the extension portion 211 may extend radially outward of the outer circumferential surface of the main body 100.

In this case, the extension portion 211 may be coupled to the outer circumferential surface of the main body 100 by, e.g., heat fusion, ultrasonic fusion, or the like, or may be attached to the outer circumferential surface of the main body 100 by a separate adhesive means (not shown) or fitted into an insertion hole (not shown) formed on the outer circumferential surface of the main body 100. Further, as the extension portion 211 is formed of a flexible biodegradable polymer material, the extension portion 211 may be freely pivoted to a position requiring latched fixation.

The locking portion 212 is formed at an end portion of the extension portion 211 and may have a hook shape in which a diameter thereof becomes smaller as it goes away from the end portion of the extension portion 211. However, the shape of the locking portion 212 is not limited thereto, and may be applied in various shapes as long as the shape of the locking portion 212 can be latched by the first organ 20 and the second organ 30. In addition, since the locking portion 212 is formed of a flexible biodegradable polymer material like the extension portion 211, the locking portion 212 may be freely pivoted to a position requiring latched fixation.

In order to more freely move the locking portion 212, a recess groove 213 may be formed between the extension portion 211 and the locking portion 212. The recess groove 213 may be a groove recessed in a thickness direction of the hook member 210 between the extension portion 211 and the locking portion 212. Since the part in which the recess groove 213 is formed is thinner than the part in which the recess groove 213 is not formed, the locking portion 212 can be easily bent in the up and down directions or easily moved in the left and right directions even by a small external force. Thus, the recess groove 213 can serve to help the locking portion 212 pivot in the up, down, left and right directions with respect to the extension portion 211.

Meanwhile, although not shown in FIGS. 1 and 2, the first organ 20 and the second organ 30 closely adhered by the fixing units 200 may be sealed by a suture unit 300 (see FIGS. 3 to 10) including a suture thread 310, a suture needle 320, and a knot 330.

Specifically, in order to seal the first organ 20 and the second organ 30 which are in close contact by the fixing unit 200, the suture needle 320 is inserted into a membrane (tissue) of the first organ 20. In this regard, the suture needle 320 is inserted into the membrane of the first organ 20 until the knot 330 is touched against an outer surface of the membrane of the first organ 20. Also, the suture needle 320, which penetrates the membrane of the first organ 20, is inserted into a membrane of the second organ 30 and then comes out again to penetrate the membrane of the second organ 30. In this case, since one end portion of the suture thread 310 is fixed to the first organ 20 by the knot 330, the tension applied to the suture thread 310 becomes larger as the other end portion of the suture thread 310 penetrating through the second organ 30 is pulled, thereby the suturing between the first organ 20 and the second organ 30 can be tight.

Although it is described as an example that the suture needle 320 is formed at one end portion of the suture unit 300 and the knot 330 is formed at the other end portion of the suture unit 300 to overcome the difficulty of forming a knot directly using the suture 320, the embodiment of the present invention is not limited thereto. For example, the suture needle 320 may be provided only at one end portion of the suture unit 300 and the other end portion may be formed at a free end, or both end portions may be provided with the suture needle 320.

Figure 3:
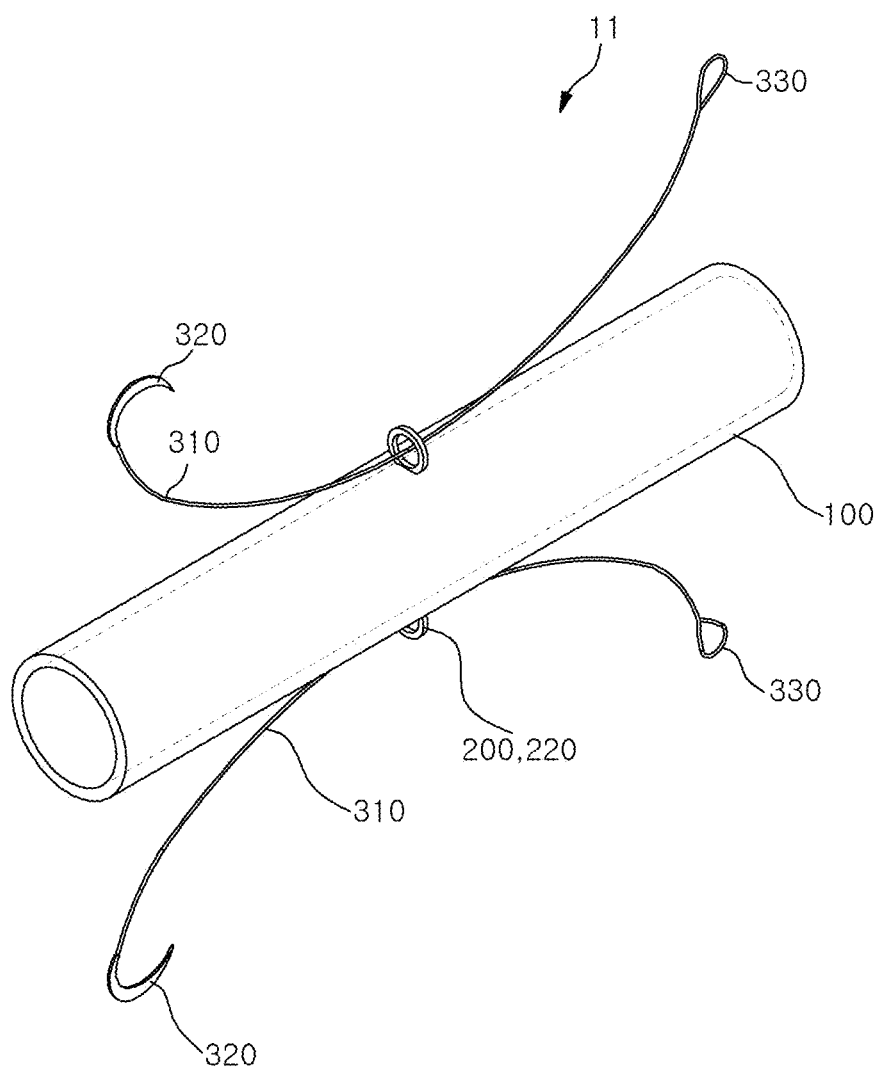
FIG. 3 is a perspective view showing a modified example of a stent for anastomosis of different kinds of organs according to the first embodiment of the present invention.
Figure 4:
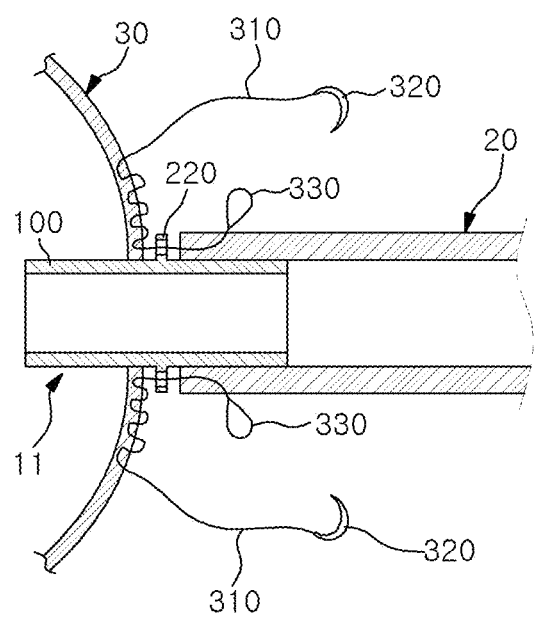
FIG. 4 is a view showing the stent for anastomosis of the different kinds of organs of FIG. 3 applied to a human body.

Further, as shown in FIGS. 3 and 4, a stent 11 for anastomosis of different kinds of organs may include a fixing unit 200 composed of a ring member 220. The suture thread 310 and the suture needle 320 that penetrate the membrane of the first organ 20 may pass through the ring member 220, and the suture thread 310 and the suture needle 320 that pass through the ring member 220 penetrate the membrane of the second organ 30.

Accordingly, as the suture thread 310 penetrating through the second organ 30 is pulled in the direction in which the suture thread 310 penetrates through the second organ 30, the tension applied to the suture thread 310 becomes larger, and thus the suturing between the first organ 20 and the second organ 30 can be tight. As such, since the suture thread 310 passes through all of the first organ 20, the ring member 220, and the second organ 30, the close contact between the first organ 20 and the second organ 30 can be maintained until the surgery is completed, for example, until the suturing between the first organ 20 and the second organ 30 are completed. For example, the ring member 220 may be formed in a ring shape having a diameter enough to allow the suture unit 300 to pass therethrough and made of a biodegradable polymer that can be melted by the body fluid and absorbed into the human body.

Figure 5:
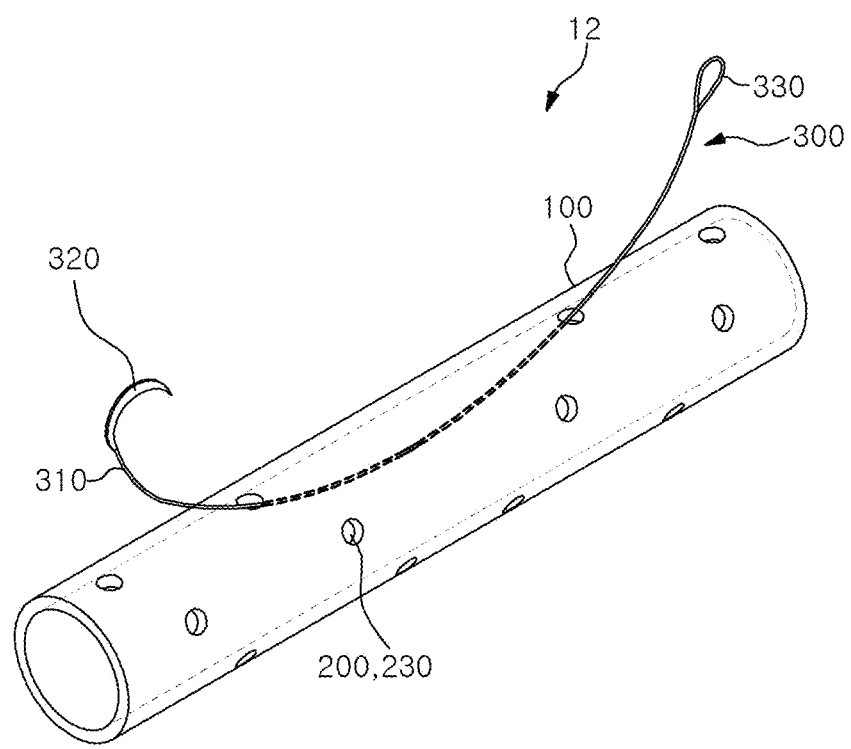
FIG. 5 is a perspective view showing another modified example of a stent for anastomosis of different kinds of organs according to the first embodiment of the present invention.
Figure 6:
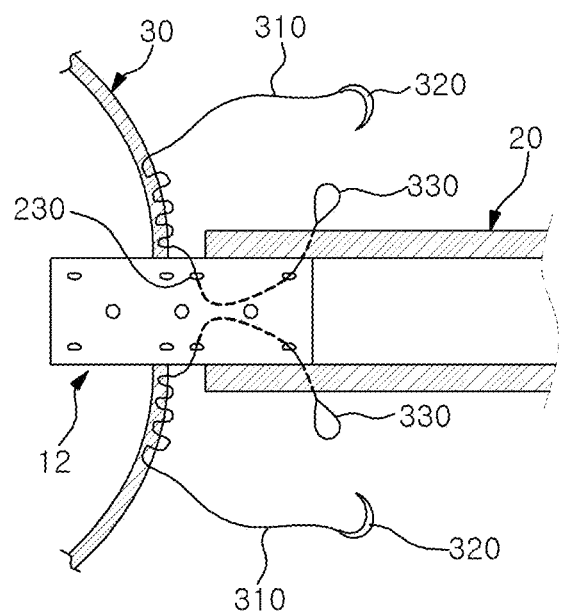
FIG. 6 is a view showing the stent for anastomosis of the different kinds of organs of FIG. 5 applied to a human body.

Further, as shown in FIGS. 5 and 6, a stent 12 for anastomosis of different kinds of organs may include a fixing unit 200 composed of a plurality of through holes 230. The suture thread 310 and the suture needle 320 that penetrate the membrane forming the first organ 20 can pass through any one of the plurality of through holes 230, and the suture thread 310 and the suture needle 320 which have passed through any one of the through holes pass through the other one of the plurality of through holes 230 again, and then penetrate the membrane forming the second organ 30.

Thus, as the suture thread 310 penetrating through the second organ 30 is pulled in the direction in which the suture thread 310 penetrates through the second organ 30, the tension applied to the suture thread 310 becomes larger, and thus the suturing between the first organ 20 and the second organ 30 can be tight. As such, since the suture thread 310 passes through all of the first organ 20, at least two through holes of the plurality of through holes 230, and the second organ 30, the first organ 20 and the second organ 30 can be maintained in close contact until the surgery is completed, for example, until the first organ 20 and the second organ 30 are completely sutured.

Figure 7:
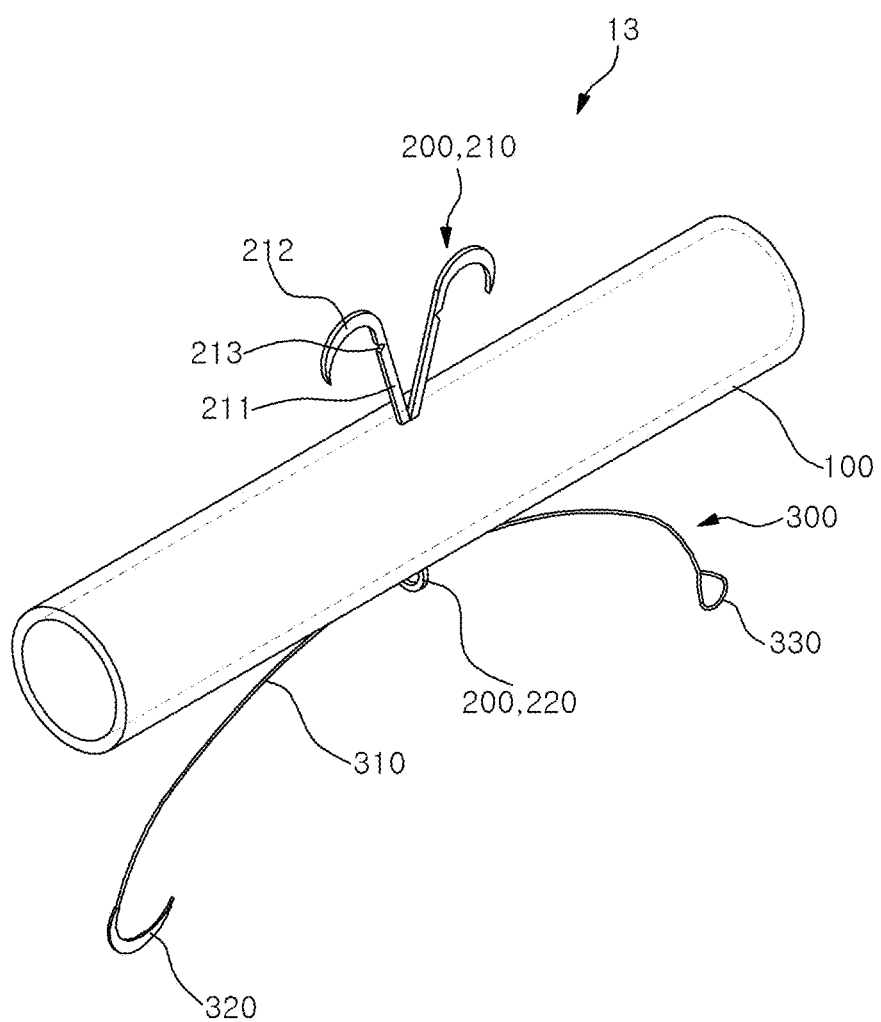
FIG. 7 is a perspective view showing still another modified example of a stent for anastomosis of different kinds of organs according to the first embodiment of the present invention.
Figure 8:
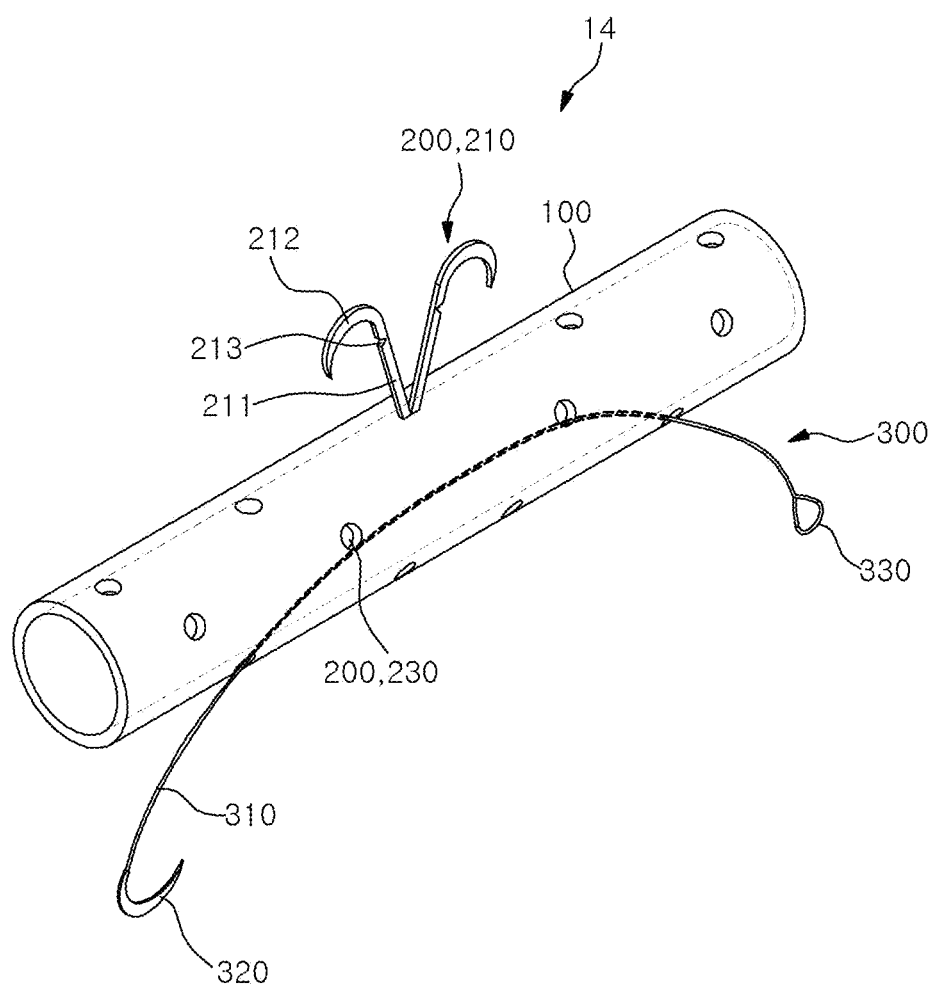
FIG. 8 is a perspective view showing still another modified example of a stent for anastomosis of different kinds of organs according to the first embodiment of the present invention.
Figure 9:
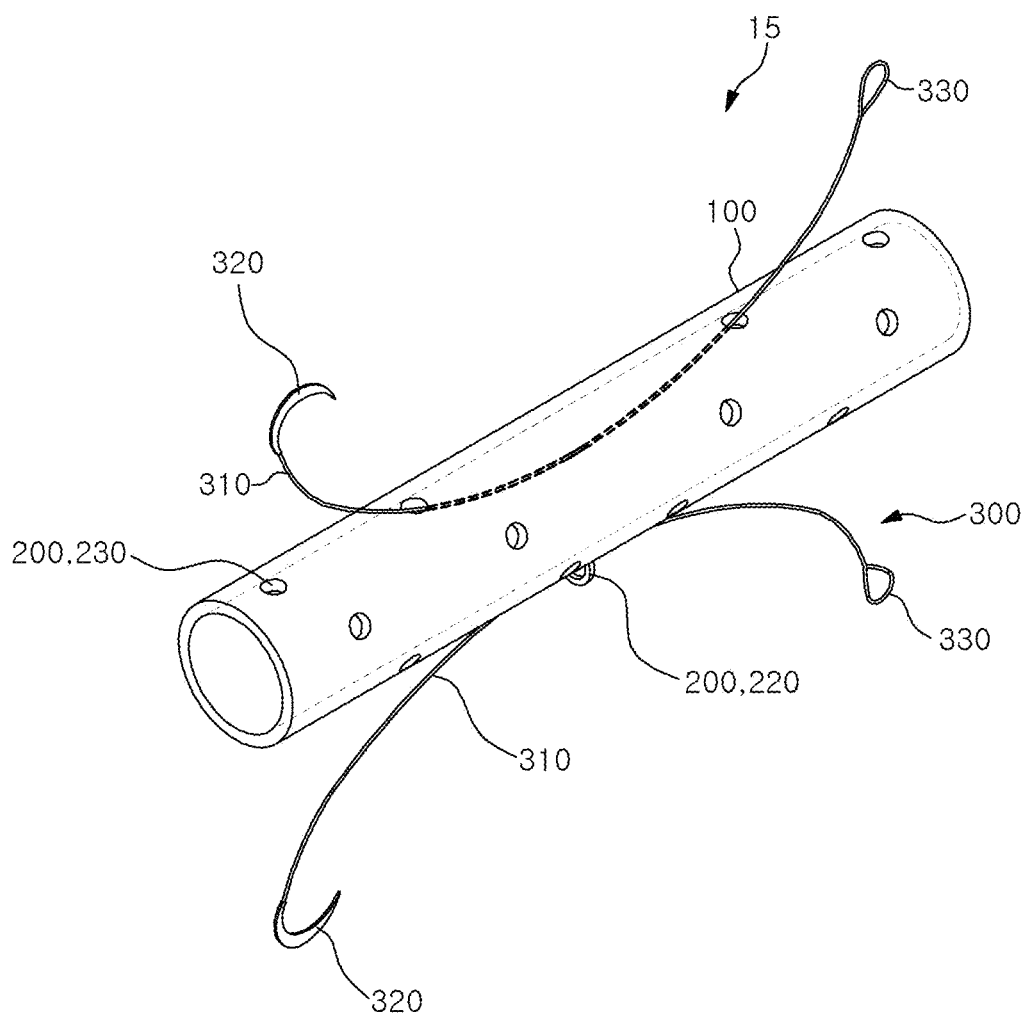
FIG. 9 is a perspective view showing still another modified example of a stent for anastomosis of different kinds of organs according to the first embodiment of the present invention.
Figure 10:
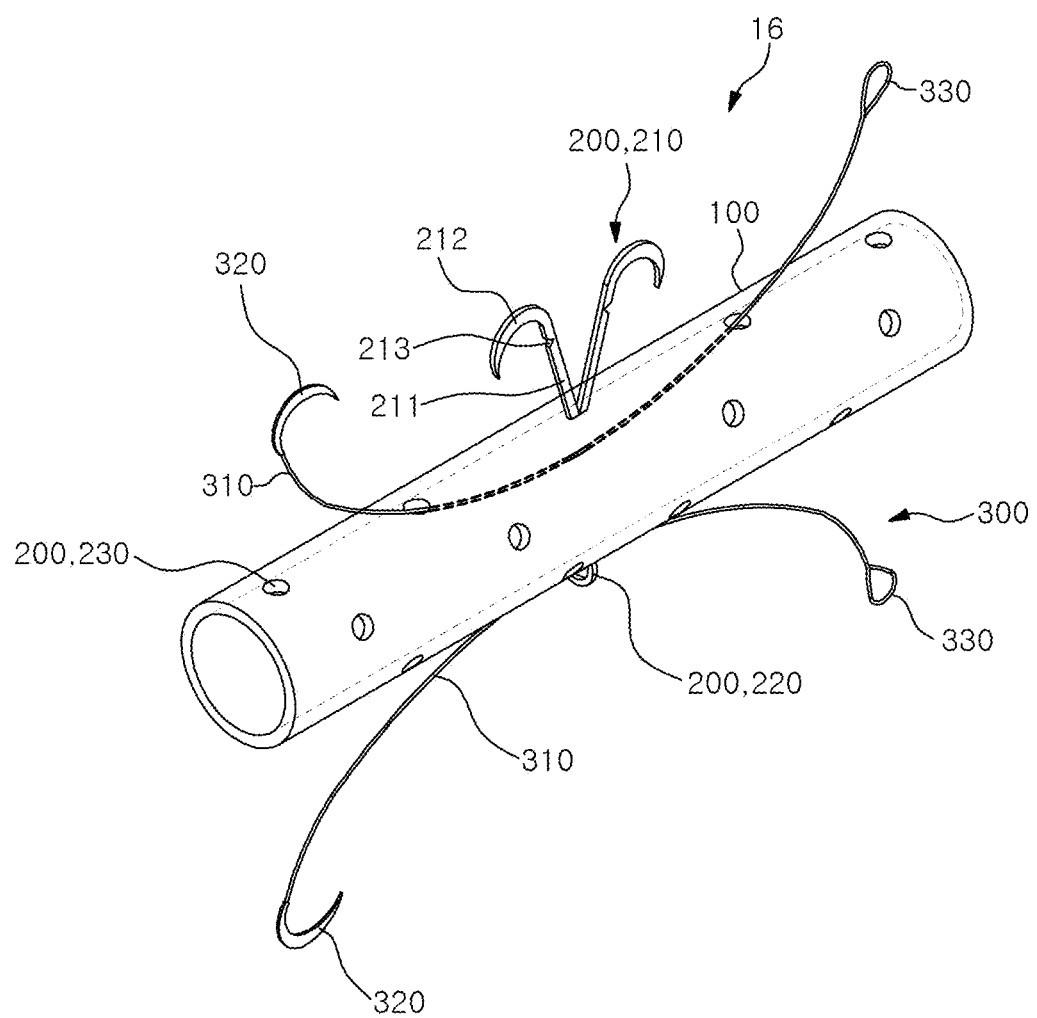
FIG. 10 is a perspective view showing still another modified example of a stent for anastomosis of different kinds of organs according to the first embodiment of the present invention.

In addition, as shown in FIG. 7, a stent 13 for anastomosis of different kinds of organs may include a fixing unit 200 having the hook member 210 and the ring member 220. Further, as shown in FIG. 8, a stent 14 for anastomosis of different kinds of organs may include a fixing unit 200 having the hook member 210 and the plurality of through holes 230. Further, as shown in FIG. 9, a stent 15 for anastomosis of different kinds of organs may include a fixing member 200 having the ring member 220 and the plurality of through holes 230. Further, as shown in FIG. 10, a stent 16 for anastomosis of different kinds of organs may include a fixing unit 200 having all of the hook member 210, the ring member 220 and the plurality of through holes 230. However, since the hook member 210, the ring member 220, and the plurality of through holes 230 have been described above, overlapping descriptions will be omitted.

Hereinafter, a stent 17 for anastomosis of different kinds of organs according to another embodiment of the present invention will be described with reference to FIGS. 11 and 12.

Figure 11:
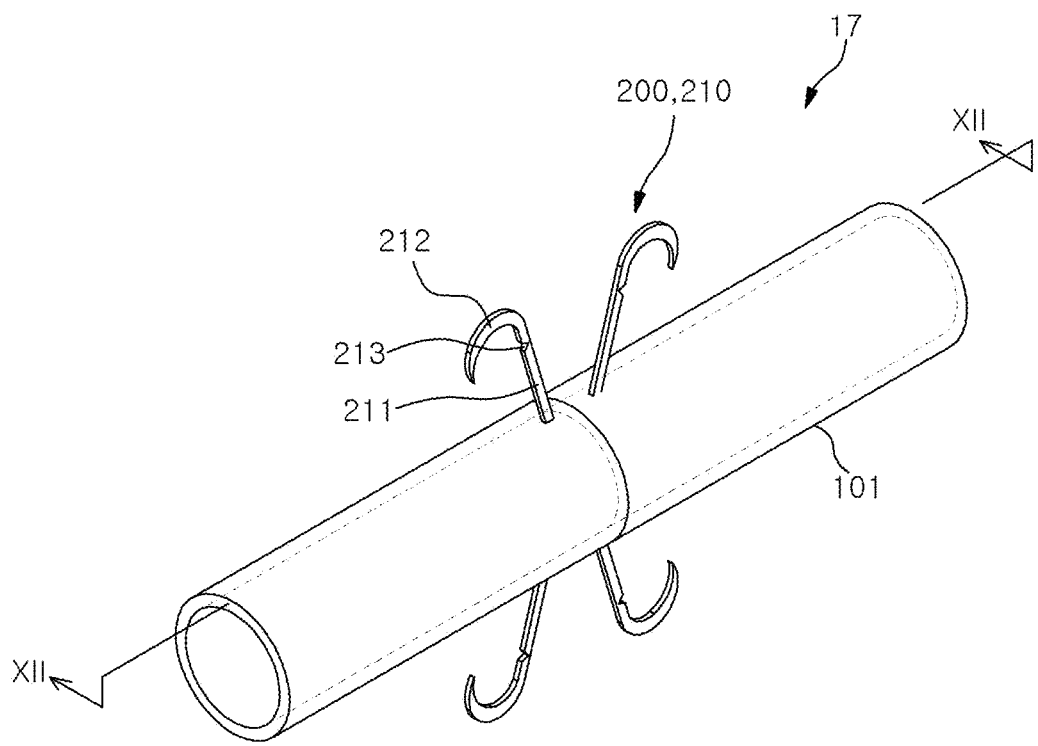
FIG. 11 is a perspective view showing an example of a stent for anastomosis of different kinds of organs according to a second embodiment of the present invention.
Figure 12:
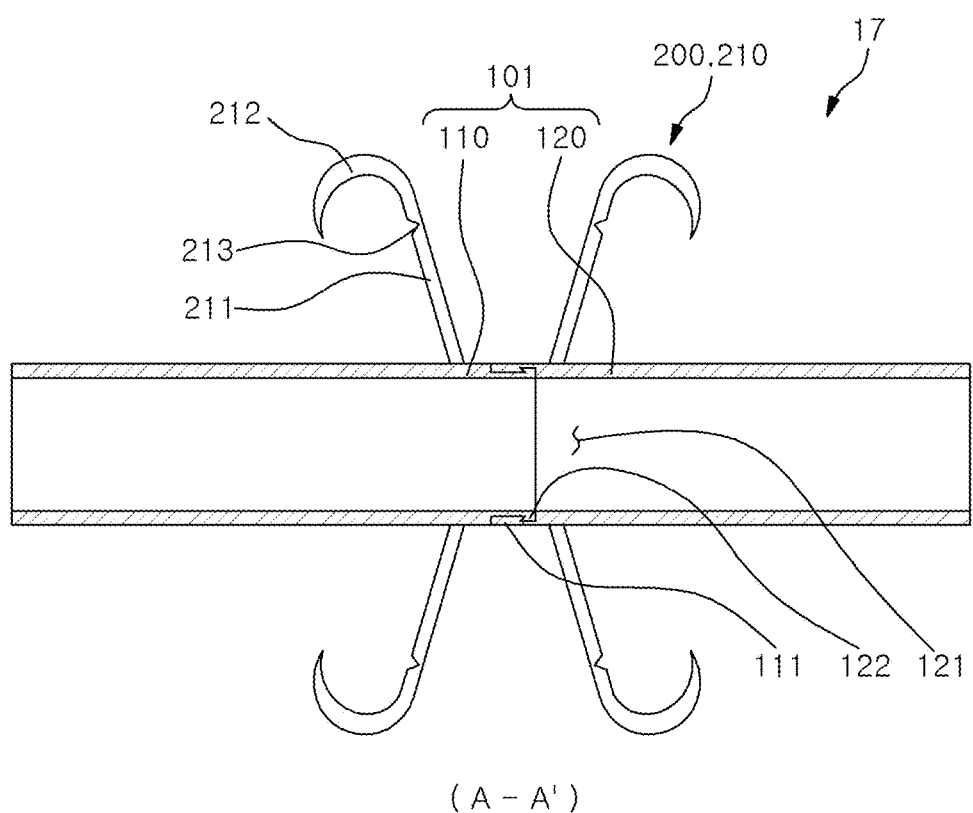
FIG. 12 is a cross-sectional view taken along the line XII-XII of FIG. 11.

Referring to FIGS. 11 and 12, the stent 17 for anastomosis of the different kinds of organs according to another embodiment of the present invention may include a main body 101 and a fixing unit 200.

The main body 101 may include a first body 110 and a second body 120 detachably coupled to the first body 110.

The first body 110 is the part to be inserted into the first organ 20, and may, e.g., be formed in a hollow cylindrical shape and made of a biodegradable polymer material.

On the other hand, locking pieces 111 may be formed to outwardly extend from a side end portion of the first body 110. In this case, the locking pieces 111 may have a hook shape whose ends extend radially outward of the first body 110, and may be made of an elastic material.

The second body 120 may be inserted into the second organ 30. For example, the second body 120 may be formed in a hollow cylindrical shape like the first body 110 and made of a biodegradable polymer material. An insertion groove 121 may be formed inside the second body 120. The Insertion groove 121 is the part provided for the insertion of the locking piece 111 and locking jaws 122 protruding inward may be provided on the inner circumferential surface of the insertion groove 121.

As such, in the process of bringing the first organ 20 and the second organ 30 into close contact with each other so as to anastomose them, the locking pieces 111 can be inserted into the insertion groove 121 and safely seated on the locking jaws 122 after overriding the locking jaws 122 by the elastic force.

Further, when the locking pieces 111 are safely seated on the locking jaw 122, the locking piece 111 are no longer moved within the insertion groove 121 so that the first organ 20 into which the first body 110 is inserted and the second organ inserted into the second body 120 are also not moved, whereby the first organ 20 and the second organ 30 can be kept in close contact with each other.

The fixing units 200 may include at least one of the hook member 210, the ring member 220, and the plurality of through holes 230. Since the description thereof has been illustrated in detail above, redundant description will be omitted.

Hereinafter, a stent 18 for anastomosis of different kinds of organs according to another embodiment of the present invention will be described with reference to FIGS. 13 to 16.

Figure 13:
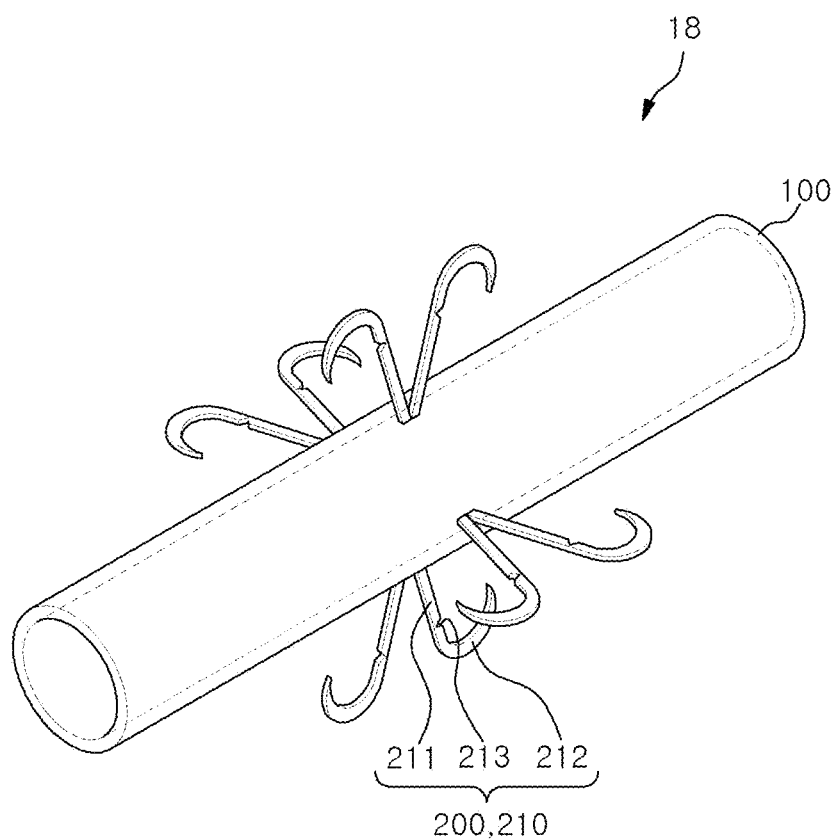
FIG. 13 is a perspective view showing an example of a stent for anastomosis of different kinds of organs according to a third embodiment of the present invention.

Referring to FIG. 13, the stent 18 for anastomosis of the different kinds of organs according to another embodiment of the present invention may include a main body 100 and a fixing unit 200.

The main body 100 has one end portion to be inserted inside the first organ 20 and the other end portion to be inserted inside the second organ 30 such that the first organ 20 and the second organ 30 communicate with each other. The main body 100 may have a hollow cylindrical shape. However, although the present embodiment illustrates as an example that the main body 100 is formed of a single body, this is nothing but an example. As illustrated in FIG. 11, the main body 100 may include the first body 110 and the second body 120 that are detachably provided from each other.

The fixing unit 200 may be provided in plurality, and the plurality of fixing units 200 may be disposed along a circumferential direction of the main body 100. In this case, the plurality of fixing units 200 may be arranged at equal intervals. Among the plurality of fixing units 200 arranged at equal intervals, two adjacent fixing units 200 in a circumferential direction of the main body 100 may be arranged to form a predetermined angle. The present embodiment illustrates as an example that the plurality of fixing units 200 are provided in the main body 100 such that the angle formed by the two fixing units 200 adjacent along the circumferential direction of the main body 100 among the plurality of fixing units 200 is 90°, but this is merely an example. If necessary, the interval between the plurality of fixing units 200 disposed along the circumferential direction of the main body 100 and the angle formed by the two fixing units 200 adjacent along the circumferential direction of the main body 100 among the plurality of fixing units 200 may be variously changed.

Figure 14:
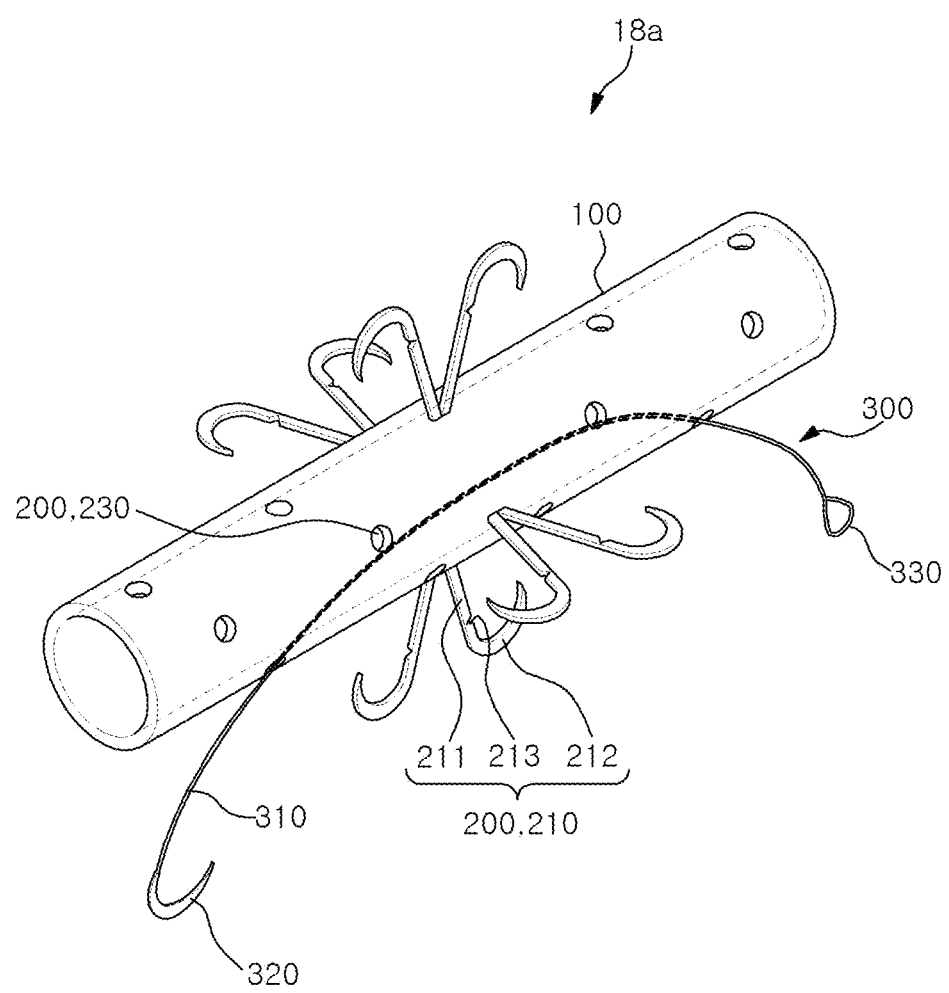
FIG. 14 is a perspective view showing a modified example of a stent for anastomosis of different kinds of organs according to the third embodiment of the present invention.

Further, a stent 18a for anastomosis of different kinds of organs may include a fixing unit 200 having the hook members 210 and the through holes 230, as shown in FIG. 14. When the first organ 20 and the second organ 30 are latched and fixed by the hook members 210, the suture unit 300 can suture the first organ 20 and the second organ 30 by passing through at least one of the plurality of through holes 230.

Figure 15:
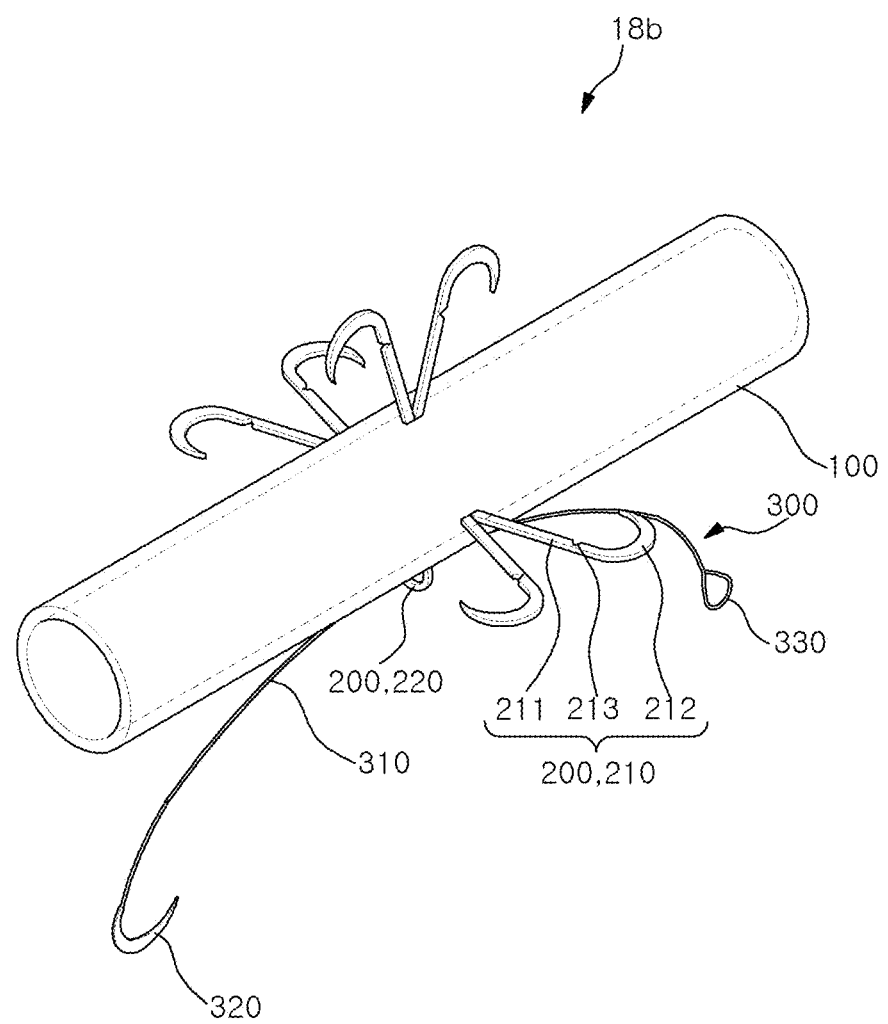
FIG. 15 is a perspective view showing another modified example of a stent for anastomosis of different kinds of organs according to the third embodiment of the present invention.

A stent 18b for anastomosis of different kinds of organs may include a fixing unit 200 having the hook members 210 and the ring member 220, as shown in FIG. 15. In this case, the hook members 210 may be arranged at equal intervals in the circumferential direction of the main body 100, and the ring member 220 may be disposed at a position facing any one of the hook members 210. When the first organ 20 and the second organ 30 are latched and fixed by the hook members 210, the suture unit 300 can suture the first organ 20 and the second organ 30 by passing through the ring member 220.

Figure 16:
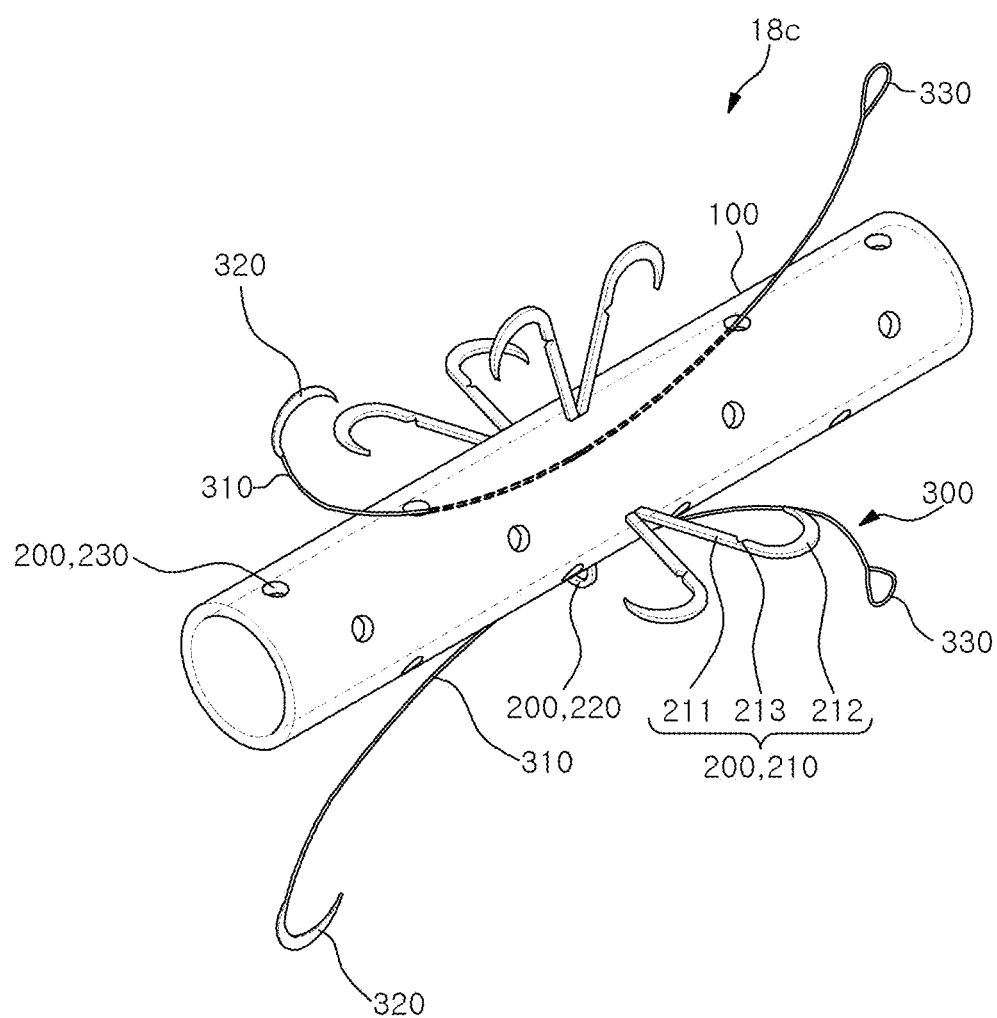
FIG. 16 is a perspective view showing still another modified example of a stent for anastomosis of different kinds of organs according to the third embodiment of the present invention.

As shown in FIG. 16, a fixing unit 200 of a stent 18c for anastomosis of different kinds of organs may include all of the hook members 210, the ring member 220, and the through holes 230. When the first organ 20 and the second organ 30 are latched and fixed by the hook members 210, the suture unit 300 can suture the first organ 20 and the second organ 30 by passing through at least one of the through holes 230 or passing through the ring member 220.

Figure 17:
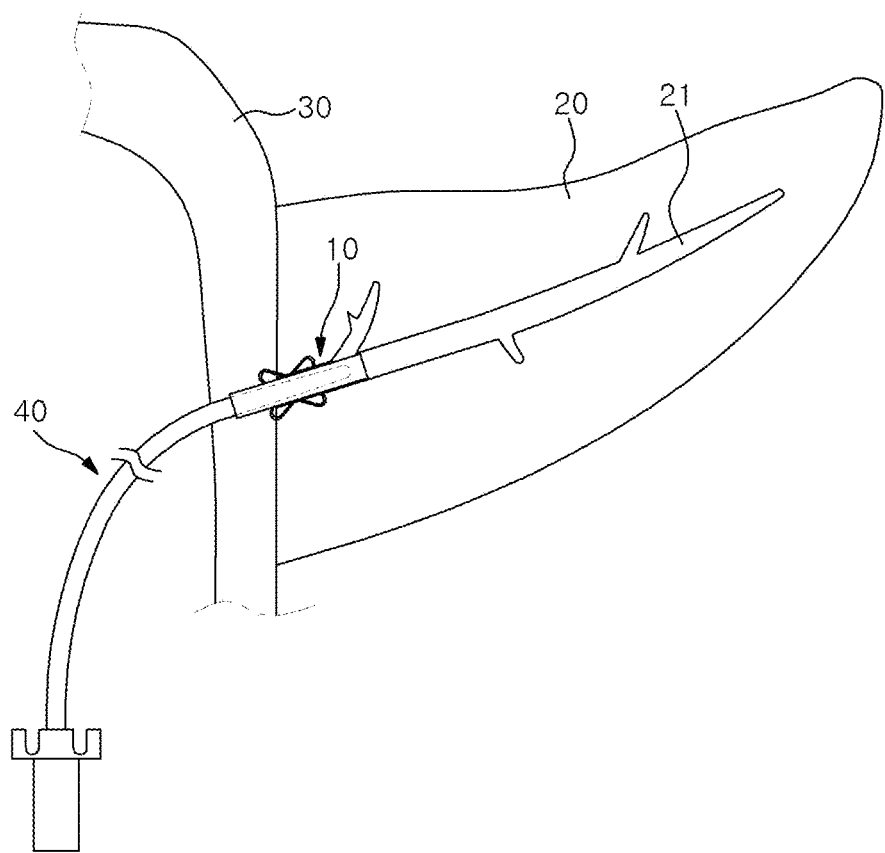
FIGS. 17 to 19 are views showing a method for anastomosing different kinds of organs using the stent for anastomosis of the different kinds of organs according to embodiments of the present invention.
Figure 18:
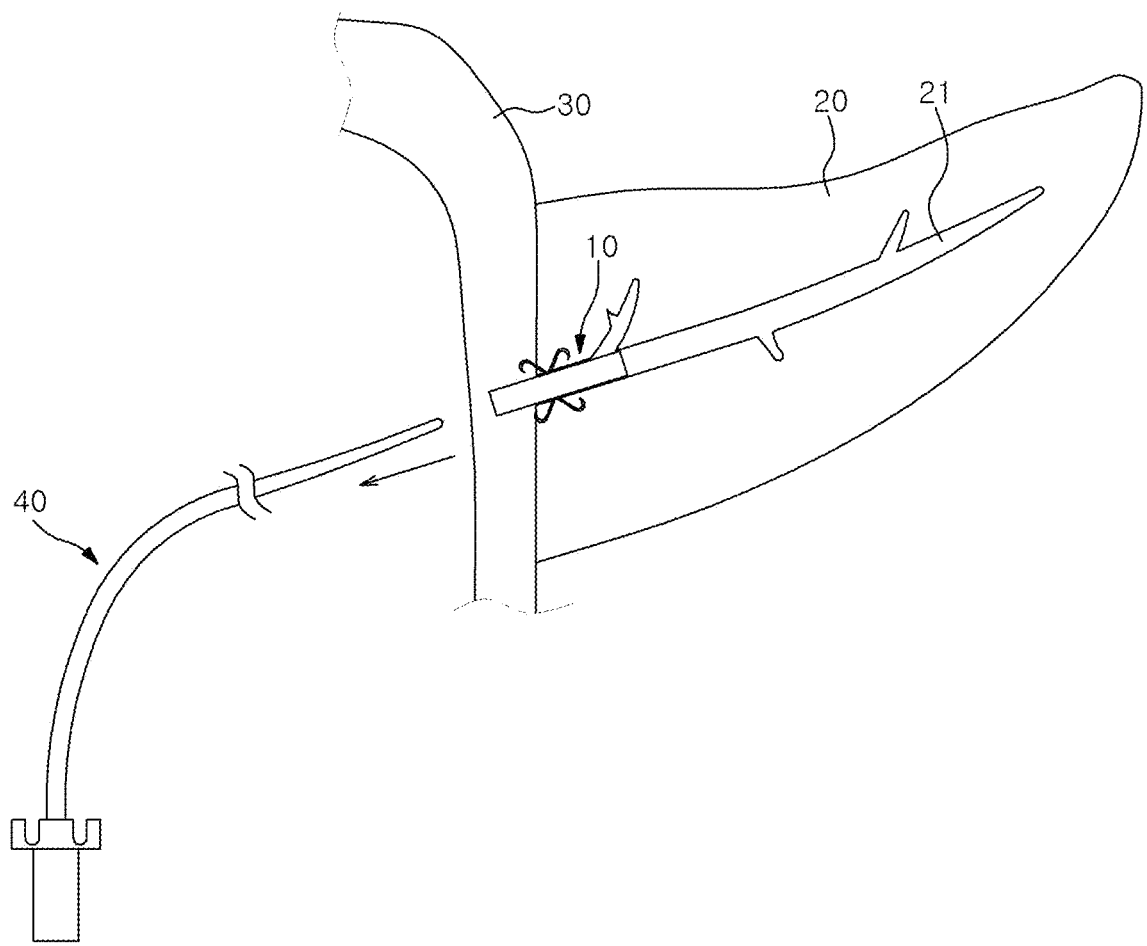
Figure 19:
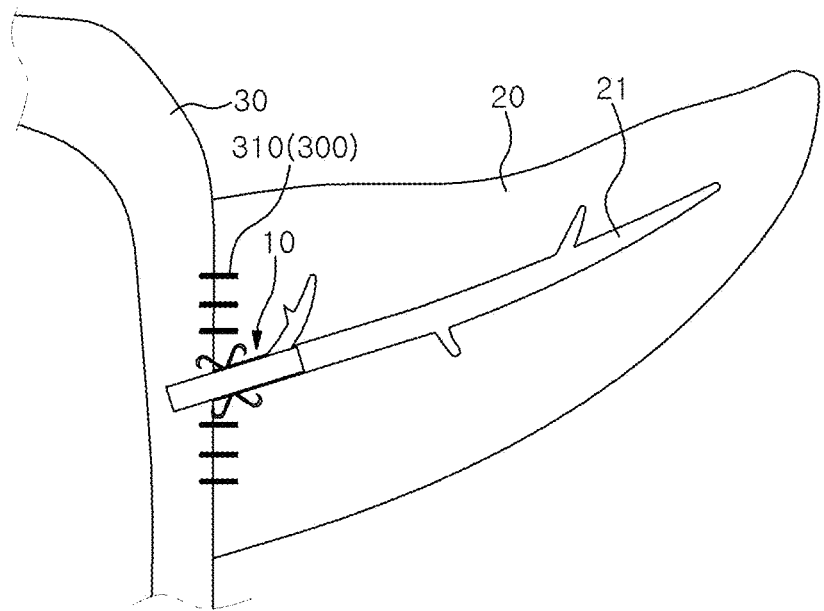

Hereinafter, referring to FIGS. 17 to 19, a method for anastomosing the first organ 20 and the second organ 30 using the stent 10 for anastomosis of different kinds of organs according to embodiments of the present invention will be described. For the convenience of explanation, a case where the first organ 20 is a pancreas and the second organ 30 is a duodenum will be described as an example. However, this is nothing but an example, and the embodiment of the present invention is not limited according to the type of the first organ 20 and the second organ 30. If necessary, the types of the first organ 20 and the second organ 30 can be variously changed. Further, although the method for anastomosing the first organ 20 and the second organ 30 will be described using the stent 10 for anastomosis of the different kinds of organs illustrated with reference to FIG. 1, this is merely an example and it is also possible to anastomose the first organ 20 and the second organ using any one of the stents 11, 12, 13, 14, 15, 16, 17, 18, 18a, 18b, 18c described with reference to FIGS. 2 to 16.

First, the stent 10 is inserted into an end portion of a separate delivery instrument 40. Next, the end portion into which the stent 10 is inserted is inserted into a pancreatic duct 21 of the first organ 20. If the main body 100 of the stent 10 is inserted into the pancreatic duct 21, the first organ 20 and the second organ 30 are respectively latched and fixed by the fixing unit provided in the main body 100 so that the distance between the first organ 20 and the second organ 30 can be maintained.

Next, after the delivery instrument 40 inserted into the pancreatic duct 21 is removed from the pancreatic duct 21 of the first organ 20, the first organ 20 and the second organ 30 are anastomosed. In this case, since the anastomosis of the first organ 20 and the second organ 30 proceeds while a gap between the first organ 20 and the second organ 30 is fixed by the fixing unit 200, the anastomosis of the first organ 20 and the second organ 30 can be performed quickly and conveniently.

The stents 10, 11, 12, 13, 14, 15, 16, 17, 18, 18a, 18b, 18c having the configurations as described above according to the embodiments of the present invention keep the first organ 20 and the second organ 30 in close contact with the fixing unit 200, whereby the first organ 20 and the second organ 30 can be anastomosed quickly and conveniently.

Further, since the main bodies 100 and 101 and the fixing unit 200 are made of a biodegradable polymer and decomposed within a human body after a predetermined period elapses, there is no need to separately remove the main bodies 100 and 101 and the fixing unit 200. Thus, the anastomosis surgery can be simplified and the costs can be saved. Further, it does not require excessive fatigue for a surgeon.

In addition, since the first organ 20 and the second organ 30 are firmly anastomosed by the fixing unit 200, surgical complications that may be caused in the anastomosed site of the first organ 20 and the second organ 30, such as leak at the anastomosed site, stenosis of the anastomosed site, inflammation, etc., can be prevented in advance.

Although the embodiments of the present invention have been described with reference to the accompanying drawings, it will be understood that any person who has an ordinary knowledge in the art to which the present invention pertains can implement the present invention in other specific forms without changing the technical spirit or essential features thereof. For example, those skilled in the art can change the material, size, etc. of each of the constitutive elements according to the application field or combine or substitute the embodiments with types which are not clearly disclosed in the embodiments of the present invention, but those embodiments will not also go beyond the scope of the present invention. Therefore, the above-described embodiments should be considered to be illustrative in all respects, not to be restrictive, and such modified embodiments will have to be included in the technical spirit described in the claims of the present invention.

What is claimed is:

1. A stent for anastomosis of different kinds of organs, comprising:
    a main body; and
    at least one fixing unit provided in the main body,
    wherein at least a portion of the main body is configured to be inserted into one of a plurality of different kinds of organs to be anastomosed with each other, and a remaining portion of the main body is configured to be inserted into another of the different kinds of organs, and
    wherein a distance between the different kinds of organs under the anastomosis is maintained by the at least one fixing unit,
    wherein the at least one fixing unit comprises one or more hook members,
    wherein the one or more hook members are provided in one or more pairs on an outer circumferential surface of the main body, and end portions of the same pair of the hook members are formed to extend in a direction away from each other,
    wherein each of the one or more hook members comprises:
    an extension portion outwardly extending from the outer circumferential surface of the main body;

a locking portion formed at an end portion of the extension portion and having a shape configured to be latched with the different kinds of organs; and a recess groove recessed from an outer surface of the extension portion and provided between the extension portion and the locking portion, and wherein the recess groove is recessed so that the locking portion is pivoted toward the main body.

2. The stent of claim 1, wherein the direction includes a longitudinal direction of the main body so that the end portions are configured to be fixedly latched to the different kinds of organs.

3. The stent of claim 1, wherein the locking portion has a hook shape in which a diameter becomes smaller as it goes away from the end portion of the extension portion.

4. The stent of claim 1, wherein the at least one fixing unit comprises a ring member installed on an outer circumferential surface of the main body to pass a suture thread for suturing a gap to be formed between the different kinds of organs.

5. The stent of claim 1, wherein the at least one fixing unit comprises a plurality of through-holes which are formed on an outer circumferential surface of the main body to pass a suture thread for suturing a gap to be formed between the different kinds of organs.

6. The stent of claim 1, wherein the at least one fixing unit comprises:

a ring member installed on an outer circumferential surface of the main body to pass a suture thread for suturing between the different kinds of organs; and a plurality of through-holes which are formed on an outer circumferential surface of the main body to pass a suture thread for suturing a gap to be formed between the different kinds of organs.

7. The stent of claim 1, wherein the at least one fixing unit comprises:

at least one of a ring member and a plurality of through-holes through which a suture thread for suturing a gap to be formed between the different kinds of organs passes, wherein the at least one of the ring member is installed on the outer circumferential surface of the main body, and the plurality of through-holes are formed on the outer circumferential surface of the main body.

8. The stent of claim 7, wherein the one or more hook members are arranged along a circumferential direction of the main body to have an equal interval between each hook member and its adjacent hook member.

9. The stent of claim 8, wherein the at least one fixing unit comprises the ring member, and wherein the ring member is arranged at a position to face the plurality of hook members.

10. The stent of claim 1, wherein the main body comprises a first body to be inserted into one of the different kinds of organs; and a second body to be inserted into another of the different kinds of organs and detachably coupled to the first body.

11. The stent of claim 10, wherein the main body further comprises:

a locking piece provided in one of the first body and the second body; and an insertion groove into which the locking piece is inserted and provided in the other of the first body and the second body.

12. The stent of claim 11, wherein a locking jaw to which the locking piece is fixedly latched protrudes from an inner circumferential surface of the insertion groove, and the different kinds of organs are maintained to make a contact with each other when the locking piece is fixedly latched to the locking jaw.

13. The stent of claim 1, wherein the main body and the at least one fixing unit comprise a biodegradable polymer including one or more species selected from a group consisting of polyglycolide, polylactide (PLLA), polylactide-glycolide copolymer (PLGA), poly p-dioxanone, polycaprolactone, trimethylene carbonate (TMC), polydioxanone-trimethylene carbonate-polyglycolide tri-block copolymer, polyhydroxyalkanoate, polypropylene fumarate, polyortho ester, polyester, polyanhydride, polyphosphazenes, polyalkylcyanoacrylate, poloxamer, polyamino L-tyrosine, modified polysaccharride, oxidized cellulose, gelatin and collagen.

14. The stent of claim 1, wherein the main body has a hollow cylindrical shape one end of which is configured to be inserted inside one of the different kinds of organs and the other end of which is configured to be inserted inside the other of the different kinds of organs to communicate between the different kinds of organs.

* * * * *